United States Patent [19]

Kowalski

[11] 4,384,474
[45] May 24, 1983

[54] METHOD AND APPARATUS FOR TESTING AND USING MEMBRANE FILTERS IN AN ON SITE OF USE HOUSING

[75] Inventor: V. Walter Kowalski, East Lyme, Conn.

[73] Assignee: AMF Incorporated, White Plains, N.Y.

[21] Appl. No.: 265,481

[22] Filed: May 20, 1981

Related U.S. Application Data

[63] Continuation-in-part of Ser. No. 202,856, Oct. 30, 1980, abandoned.

[51] Int. Cl.³ .................. B01D 39/00; G01L 19/00
[52] U.S. Cl. .................... 73/38; 73/432 R; 210/95
[58] Field of Search .......... 73/38, 432 V; 210/95, 210/433.2, 188

[56] References Cited

U.S. PATENT DOCUMENTS

| | | | |
|---|---|---|---|
| 2,432,814 | 12/1947 | Schmidt | 73/45.5 |
| 3,039,293 | 6/1962 | Reddick et al. | 73/38 |
| 3,293,431 | 12/1966 | Bennett et al. | 73/38 X |
| 3,336,793 | 8/1967 | Tuttle | 73/38 X |
| 3,478,601 | 11/1969 | Niebergall | 73/38 X |
| 3,505,876 | 4/1970 | Niebergall | 73/38 X |
| 3,757,947 | 9/1973 | Wakefield et al. | 210/95 X |
| 3,824,823 | 7/1974 | Pontello | 73/38 X |
| 3,876,738 | 4/1975 | Marinaccio et al. | 264/41 |
| 3,977,253 | 8/1976 | Lewis | 73/38 |
| 4,120,794 | 10/1978 | Taylor | 210/345 |
| 4,184,966 | 1/1980 | Pall | 210/493 B |
| 4,218,313 | 8/1980 | Aid et al. | 210/95 X |

Primary Examiner—Daniel M. Yasich
Attorney, Agent, or Firm—David E. Dougherty; Charles J. Worth

[57] ABSTRACT

An improved method and apparatus for controlled pressure testing at least one membrane filter in an on site of use housing, and to simultaneously test a plurality of membrane filters in a covered common housing at the site of use to independently determine by visual flow indicators if each filter is acceptable for use or is defective.

22 Claims, 3 Drawing Figures

METHOD AND APPARATUS FOR TESTING AND USING MEMBRANE FILTERS IN AN ON SITE OF USE HOUSING

This application is a Continuation-In-Part of my U.S. application Ser. No. 202,856, filed Oct. 30, 1980 and now abandoned.

The present invention relates generally to testing membrane type filters and more particularly to a novel method and apparatus for testing membrane filters in an "on site of use" housing.

The specific construction of the membrane filter means disposed within the "on site of use" housing is not to be construed as a limitation of the present invention. The filter means may be a suitably supported disc-type membrane or a membrane type filter cartridge. The present invention also contemplates simultaneously testing multiple membrane type filter cartridges and determining which, if any, individual cartridge is not suitable for use; such cartridges being of unique design.

Membranes are being employed in the filtration of liquids where sterility must be assured and bacteriological organisms must be removed. This is normally accomplished by using membranes in the microporous range such as disclosed in U.S. Pat. No. 3,876,738. Users of membrane filters require validation of the filters before, during and after product filtration, and it is necessary to prevent any contamination from being introduced from outside sources. This dictates the importance of on site of use testing without creating outside sources of contamination. In methods according to the prior art it has normally been necessary to use accessory equipment such as graduated cylinders, flasks, pans, hoses, etc., all of which are extraneous to the fixed on site installation. Various membrane filter tests used up to this time by industry are described in an article entitled "Non-Destructive Tests For Bacterial Retentive Filters" by Ben Trasen which was published in the September/October 1979 issue of the Journal of Parental Drug Association, pages 273 to 279.

The applicant knows of no prior art method of simultaneously testing multiple membrane filter cartridges and individually validating or positively determining which one of the several cartridges is defective in a multi-cartridge housing. However, industry has been using multiple membrane cartridges within a single housing and, to avoid unnecessary contamination, has been batch testing the cartridges at the point of use in a manner noted above. It should be appreciated that membrane cartridges are costly and with the batch test methods presently in use, all of the cartridges in a single housing are probably discarded when there may be only one which is bad.

Accordingly, one object of the present invention is to provide an improved method and apparatus for integrity testing membrane filters at the site of use.

Another object of the present invention is to provide a method and apparatus which requires no extraneous equipment and once the connections to the housing have been made and the housing has been closed, the integrity of the filter unit during test and use is not disturbed unless a defective membrane filter must be replaced.

Still another object of the present invention is to provide a method and apparatus wherein a plurality of membrane filters are simultaneously tested within a single housing.

And another object of the present invention is to provide a method and apparatus with means for determining whether each of the membrane filters is acceptable for use.

And another object of the present invention is to provide a method and apparatus with permanent inlet and outlet connections for both the test liquid and the liquid to be filtered, and inlet and outlet connections remaining undisturbed when a membrane filter is replaced.

Still another object of the present invention is to provide a novel membrane filter cartridge with its core open at both ends during use of the cartridge.

And still another object of the present invention is to provide a membrane filter cartridge with redundant sealing means at its ends.

The foregoing and other objects and advantages will appear more fully hereinafter from a consideration of the detailed description which follows, taken together with the accompanying drawing, wherein several embodiments of the invention are illustrated by way of example. It is to be expressly understood, however, that the drawings are for illustration purposes only and are not to be construed as defining the limits of the present invention.

FIG. 1 of the drawings is an elevational view of a multi-cartridge filter with portions thereof broken away to better illustrate the present invention.

Figure 1:
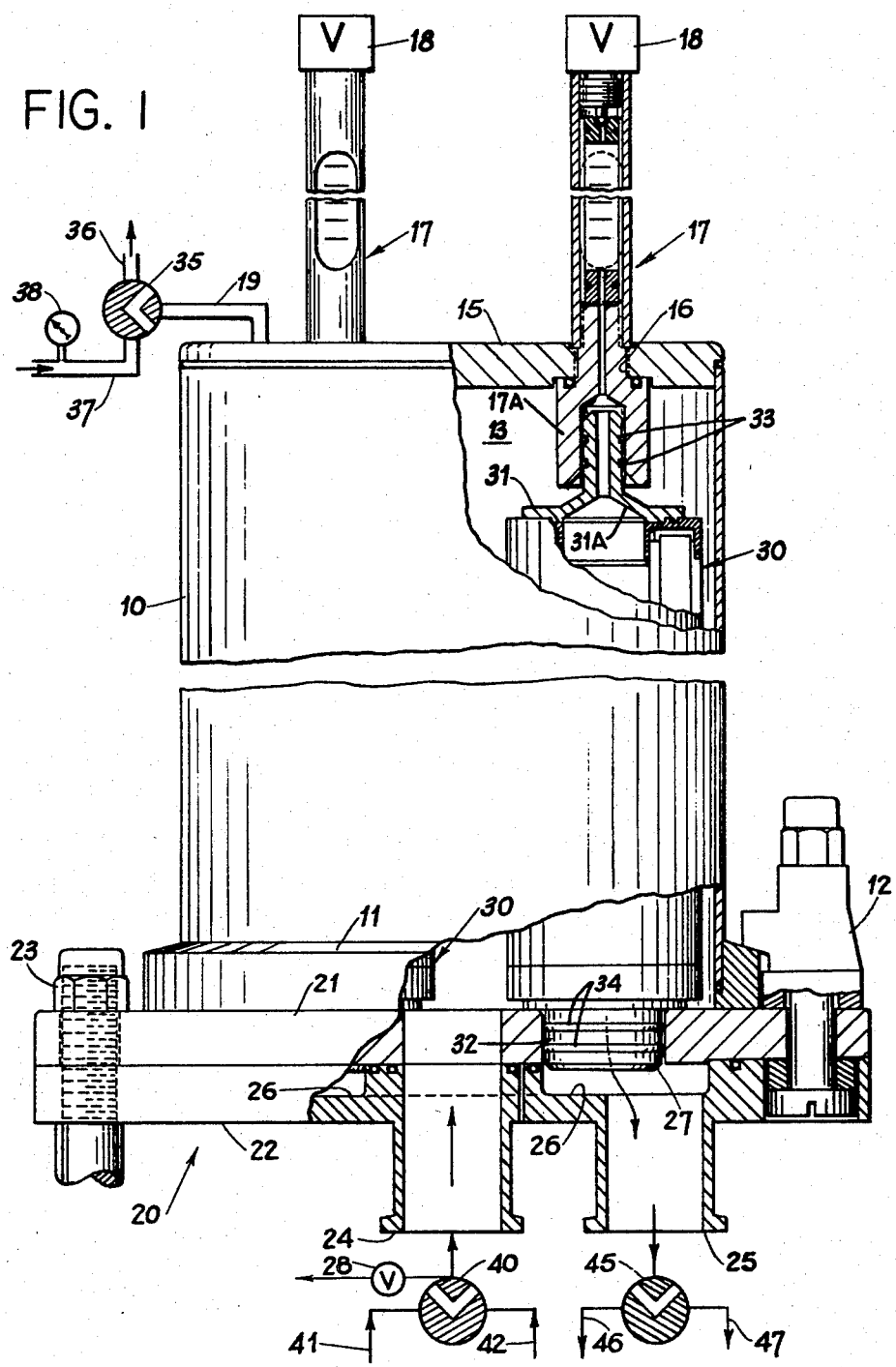

While only a multi-cartridge housing is shown in FIG. 1 of the drawings, a showing of a single cartridge and housing would be mere duplication of the illustration provided. For clarity, the novel invention will be described and discussed in connection with multi-cartridges in a single housing. When applied to a single cartridge in a single cartridge housing, duplication of parts and manifolding for multi-cartridges would not be required, as will be further discussed.

It also is to be understood that membrane cartridges as used herein is intended to mean any cartridge type filters having membrane filter media. To facilitate description, three-way valves are employed to alternatively connect test liquid or liquid to be filtered to the inlet and outlet which may also be closed by such valves. A three way valve is also employed to alternatively close or connect the filter chamber within the housing to atmosphere for venting or to control air pressure as may be required. It is considered to be merely a matter of choice to employ such three way valves or to use separately valved line connections.

Referring now to the drawings, and more particularly to FIG. 1, the novel apparatus is provided with a housing comprising tubular cover 10 having a flange ring 11 for releasably connecting the cover at its lower end to a base 20 by a series of releasable connector or fastening means 12 (only one being shown). The upper end of the cover 10 is closed by a top plate 15 having a plurality of openings 16 with sockets or adaptors 17A for mounting visual flow condition indicating means such as sight glasses or gages 17. Each glass or gage 17, which is provided at its inner end with a socket or adaptor 17A, is provided at its outer end with a valve 18 the function of which will be further discussed. It should be noted that the sockets or adaptors provide flow communication between the upper portion of the filter chamber 13 and the indicating means or sight glasses 17.

The housing comprising the cover 10 and base 20 defines a filter chamber 13 which is provided with a port or flow path 19 in communication with the upper portion of the filter chamber 13. The flow path 19 is provided to vent the filter chamber 13 to atmosphere and, at particular times as required for operation, is adapted to be selectively closed and connected to a source 37 of controlled air pressure having a gage 38 for instantaneously indicating pressure of the controlled air, preferably by provision of a three way valve 35 having a vent connection or port 36, as shown.

The base 20 is formed by an inner plate 21 and an outer plate 22 joined together in face to face relationship by a series of fasteners 23 (only one shown). The plates 21 and 22 are provided with axially aligned central openings defining an inlet 24 for the filter chamber 13. The outer plate 22 is further provided with a recess 26 forming a manifold which provides communication between an outlet 25 in the outer plate 22 and a plurality of sockets or socket openings 27 through the inner plate 21. The openings 27 are equal in number and are axially aligned with the openings 16 in the upper plate 15 or with the sockets or adaptors 17A for the sight glasses or indicating means 17. The inlet 24, at particular times as required for operation, is adapted to selectively receive test liquid and liquid to be filtered, and also be closed or connected to drain the chamber 13; while the outlet 25, at particular times as required for operation, is adapted to be selectively closed, connected to discharge test liquid and to discharge filtered liquid. This is preferably accomplished by providing three way valve 40 to close the inlet 24 in one position or to connect the inlet to a source 41 of test liquid or a source 42 of liquid to be filtered. Similarly, a three way valve 45 is provided to close outlet 25 or to connect the outlet to a discharge line 46 for test liquid or to a discharge line 47 for filtered liquid. A suitable valved drain or drain valve 28 for the filter chamber 13 is provided adjacent the valve 40, as shown, or valve 40 may be made to provide a drain position. Alternatively, filter chamber 13 can be fully drained by removing pressure from inlet line 41 for test liquid which is connected to inlet 24 by the valve 40, and, opening valve 35 to vent.

A plurality of membrane cartridges 30 of generally conventional basic construction are provided in the filter chamber 13 except for each having a unique upper end cap or cap assembly 31 sealing the top end of the membrane and extending or being plugged into the socket 17A of a sight glass 17. Each end cap 31 is provided with redundant socket seal means in the form of a pair of axially spaced O-rings 33 to prevent leakage through the connection from the chamber 13. Similarly, each cartridge 30 is provided with a lower end cap or cap assembly 32 sealing the bottom end of the cartridge membrane and extending into or being plugged into an appropriate socket opening 27 axially aligned with the socket 17A of a sight glass or indicating means 17 receiving the upper end cap 31. The lower end cap 32 is also provided with redundant sealing in the form of a pair of axially spaced O-rings 34. It should be particularly noted that the core within the membrane of each cartridge is open at both ends, and communicates at its upper end through end cap 31 with a sight glass or indicating means 17 and at its lower end through end cap 32, the appropriate socket 27 with the manifold 26 and outlet 25. Adding to the unique construction of the cartridge 30, the upper end cap 31 is provided with a tapered or conical inner surface 31A which connects a flow path portion of larger diameter receiving the upper end of the cartridge core and assists or permits air bubbles to rise unimpeded from the cartridge core through a flow path portion of smaller diameter into the indicating means or sight glass 17.

In an arrangement having only a single cartridge 30 in a single cartridge housing, only one opening 16 for a single adaptor 17A and sight glass 17 would be required. The manifold 26 would be eliminated and a single socket opening 27 would be aligned with the outlet 25 in a manner similar to the inlet 24. In effect, it would be preferable to eliminate the inner plate 21 from the base 20 and the outlet 25 would be axially aligned with the single opening 16. In this instance, the outlet 25 would be a socket and receive the lower end cap 32 of the single cartridge 30.

It should be noted that the vent 19 and the inlet 24 are in flow communication with the chamber 13 on the inlet side of or surrounding the membranes of the cartridges 30 which is considered as being the inlet chamber area. The cores of the cartridges 30 on the opposite side of the membranes, with or without the manifold 26, are considered as being the outlet chamber area in flow communication with the sight glasses or indicating means 17 and the outlet 25.

In the absence of liquid in the apparatus and with valves 18, 28, 35, 40 and 45 all closed, fasteners 12 can be rotated to release the flange 11 and cover 10 can be removed from the base 20. An appropriate number of cartridges 30 are put into the cover 10 with the upper end caps 31 each being inserted or plugged into the inner end or socket member 17A of a different one of the sight glasses or gages 17 while the lower end caps 32 are inserted or plugged into the appropriate axially aligned sockets or socket openings 27 in the base 20. The cover 10 is then reclamped to the base 20 by fasteners 12 and the apparatus is prepared for testing the membrane cartridges 30.

Initially, valve 35 is opened to vent the inlet area of chamber 13 through lines 19 and 36, and valve 40 is operated to gradually connect line 41 from a source of test liquid or wetting fluid to the inlet 24 for filling the inlet area of the chamber 13. When the test liquid starts to escape from the vent 36, the valve 35 is closed and valve 45 is opened to connect the outlet 25 to the test liquid return line 46 providing a controlled circulating flow of test liquid through the cartridges 30 to wet the membranes thereof and fill the outlet area of the filter chamber 13 with test liquid. One by one the valves 18 are opened unless they are self venting, to fill the sight glasses or indicating means 17 with test liquid and are closed as each of the sight glasses are filled. The flow rate of the test liquid can be controlled by manipulation of valves 40 and 45 but normally the test liquid circulating system would be provided with valves (not shown) particularly for this purpose. At this time, the filter chamber 13, cartridges 30 and indicating means or sight glasses 17 are all filled with test liquid.

Circulating flow of test liquid through the cartridges 30 is maintained for a nominal period of time to assure that the membranes or membrane filter media of the cartridges 30 are sufficiently wet. The inlet 24 is now closed by the valve 40 and a nominal pressure of about 5 psig is provided to the inlet area of the chamber 13 by connecting line 19 to line 37 by valve 35; line 37 being connected to a compressed air or gas source as previously stated. The nominal pressure will cause continued flow of test liquid through the cartridges 30 from the inlet area to the outlet area until all but a thin layer of liquid remains at the bottom of the inlet area of the chamber 13.

If during the period nominal pressure is being provided to chamber 13 by monitoring the indicating means it is noted that air bubbles appear in one of the indicating means or sight glasses 17 causing the liquid level in the indicating means sight glasses to drop which is an indication of a defective cartridge 30, the test either can continue by appropriate manipulation of valve 18 of that indicating means or sight glass and the outlet valve 45 to control flow and maintain a liquid level in the defective cartridge sight glass, or the test can be terminated. The defective cartridge 30 would then be replaced and a retest performed.

When essentially all flow of test liquid through outlet line 46 has stopped, valve 45 is closed, all valves 18 are opened and the air pressure to filter chamber 13 from the source 37 of controlled air is gradually increased to the diffusional flow rate test pressure when air passes through the membranes and intermittently bubbles into the sight glasses 17 escaping through the open valves 18. The intermittent escape of air bubbles should be essentially the same in all of the sight glasses or indicating means 17. Excessive bubbling in any of the sight glasses 17 would indicate a defective cartridge 30 which is in communication with the sight glass exhibiting excessive bubbling.

To determine the diffusional flow rate, valves 18 are closed and valve 45 is opened connecting outlet 25 to line 46. Intermittent air bubbling into the sight glasses 17 will cause the liquid levels therein to drop. This measured drop is timed to calculate the diffusional flow rate. If the calculated diffusional flow rate is less than the maximum allowable diffusional flow rate, the cartridge is acceptable.

If it is desired to determine the foam all over point of a membrane cartridge 30, air pressure is gradually increased until air bubbles replace the test liquid from the indicating means or sight glasses 17 almost instantaneously, and the pressure of gage 38 will provide the foam all-over point. The air pressure should be maintained until all test liquid is expelled from the outlet area of the chamber 13 on downstream side of the membrane media of the cartridges 30.

After tests are completed and all cartridges 30 are acceptable for use, there will be a thin layer of test liquid or wetting fluid in the bottom of the inlet area of the chamber 13 of a depth approximately equal to the height of the bottom end caps 32 of the cartridges 30. Since all of the test liquid will have been drained from the sight glasses 17 and cartridges 30, with valves 18 and 45 closed, the valve 35 is opened to vent the inlet area of the chamber 13 and valve 28 is opened to drain all the test liquid remaining at the bottom of the inlet area of chamber 13 through the inlet 24. After draining is complete, the valves 35 and 28 are closed and filtering can commence without further delay by connecting inlet line 42 for liquid to be filtered to the inlet 24 by valve 40 and discharge line 47 for filtered liquid to outlet 25 by valve 45. During filtration, appropriate manipulation of the inlet valve 40 and the outlet valve 45 can control the flow rate or the system can be provided with automatic flow control means.

It should be readily understood that when the filter unit has but a single filter cartridge 30, there will be only one visible indicating means 17 with its vent valve 18. Testing of such a unit will be as previously described with only the single indicating means 17 being monitored and controlled by its valve 18.

Figure 2:
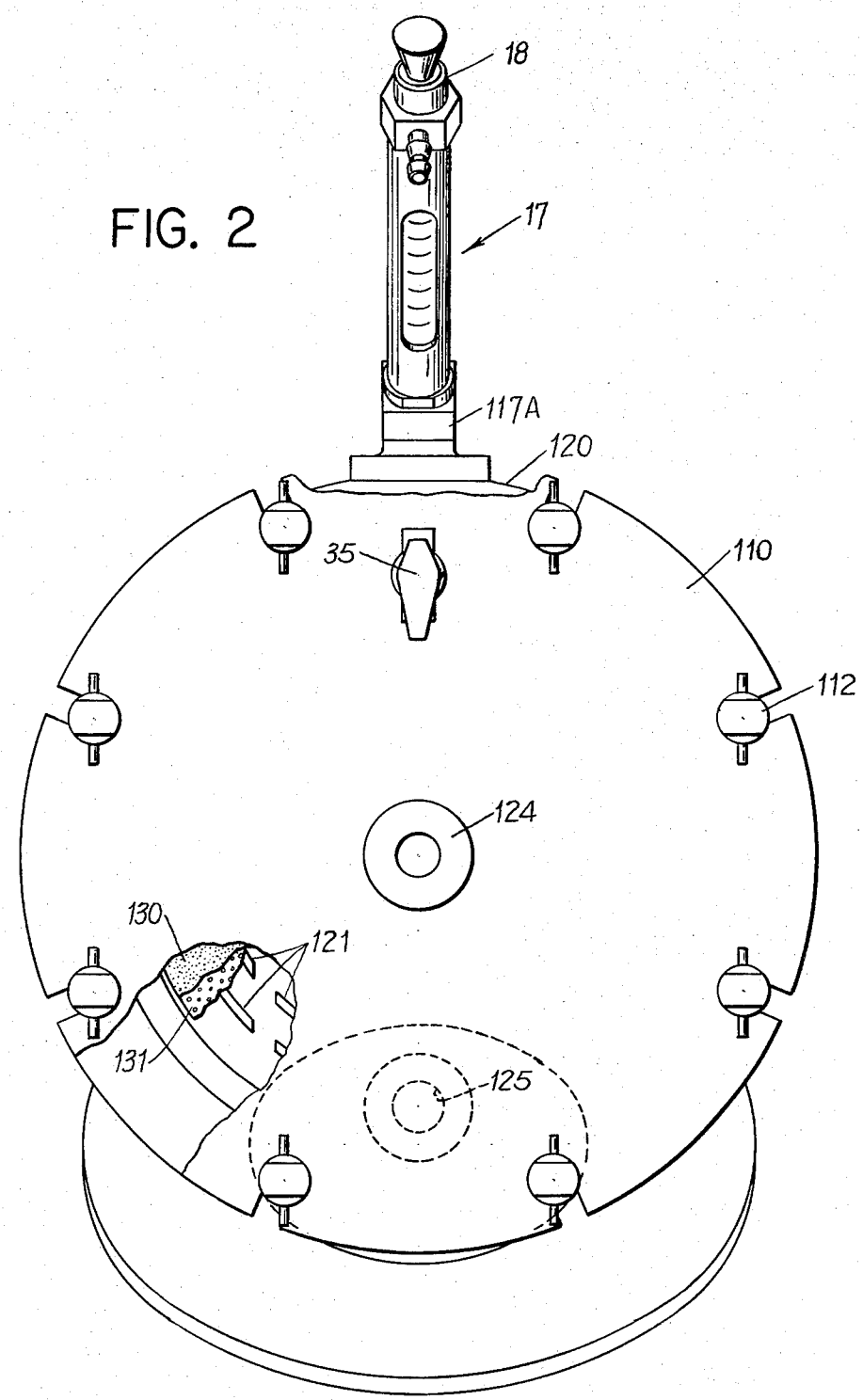
FIG. 2 is an elevational view of a filter in accordance with the present invention having a disc type membrane for the filter media therein.
Figure 3:
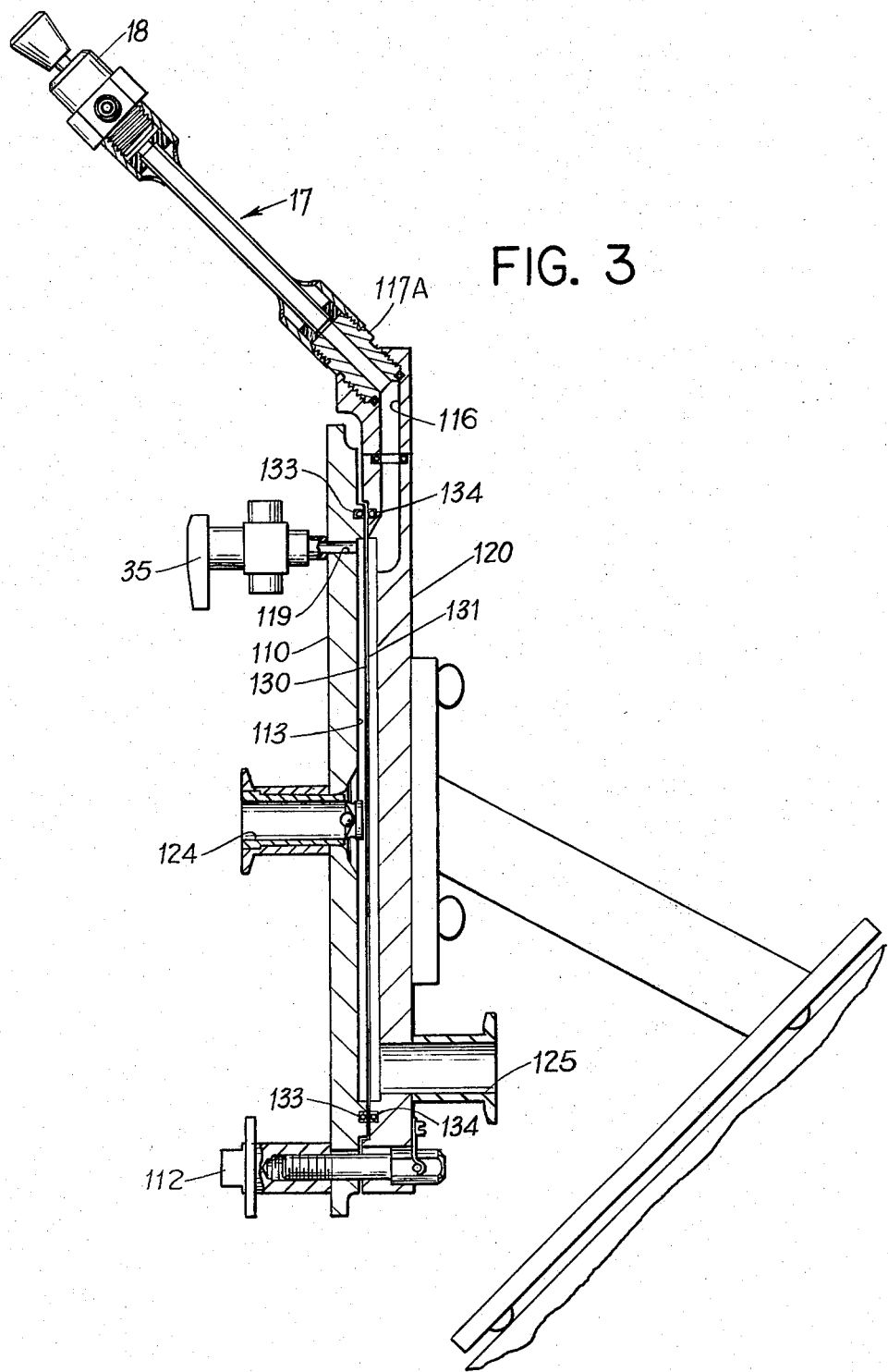
FIG. 3 is a sectional view taken on line 3—3 of FIG. 2.

Referring now to FIGS. 2 and 3, a modified housing is comprised of a cover 110 and a base 120 corresponding to the cover 10 and base 20, respectively, of FIG. 1. The cover 110 and base 120 are releasably connected together by fastening means 112, and are formed to define a filter chamber 113 corresponding to chamber 13. In place of the membrane filter cartridges 30 of FIG. 1, a disc-type membrane filter 130 with a suitable porous or perforated backing plate or sheet 131 is disposed in and divides the chamber 113 into inlet and outlet areas. The peripheries of the membrane 130 and backing plate or sheet 131 are retained or clamped between the cover 110 and base 120, and are provided thereat, as shown, with O-ring seals 133 and 134.

An inlet 124, in communication with the inlet area of the filter chamber 113, corresponds to the inlet 24 and is adapted for similar flow control by the valve 40 while an outlet 125 in communication with the outlet area of the filter chamber 113, corresponds to the outlet 25 and is adapted for similar flow control by the valve 45. The cover 110 is provided with a vent port 119, corresponding to the flow path 19, in communication with the inlet area at the upper portion of the filter chamber 113 and is adapted for selective flow control by the valve 35. The modified housing also is provided with an opening or flow path 116 corresponding to one of the openings 16, and a socket or adaptor 117A corresponding to the socket 17A. The socket 117A mounts a sight glass or visible indicating means 17, and with openings 116, provides communication for the visible indicating means 17 with the outlet area at the upper portion of the filter chamber 130.

The base 120 is preferably provided with a plurality of ribs 121 which extend into the outlet area of filter chamber 113 to engage and support the backing plate or sheet 131 against deflection due to pressure differentials across the filter membrane 130.

This modified filter will be tested and used in the same manner as previously described relative to the filter of FIG. 1 when only a single filter cartridge 30 is tested and used.

Although several embodiments of the invention have been illustrated and described in detail, it is to be expressly understood that the invention is not limited thereto. Various changes may be made in the design and arrangement of the parts without departing from the spirit and scope of the invention as the same will now be understood by those skilled in the art.

What is claimed is:

1. Apparatus for integrity testing and using membrane filter means at the site of use, comprising
    a base and a cover releasably connected to said base thereby forming a housing which defines a filter chamber;
    a membrane filter disposed within said housing and dividing the filter chamber into an inlet area on one side of said membrane filter and an outlet area on the opposite side of said membrane filter;
    said housing having an inlet in communication with the inlet area of said chamber, an outlet in communication with the outlet area of said chamber and vent means communicating with said inlet area at the upper portion of said chamber;

said inlet adapted at particular times to be selectively closed, connected to a source of test fluid during test of said membrane filter and to a source of fluid to be filtered during use of said membrane filter;

said outlet adapted at particular times to be selectively closed, connected to a return line for said test fluid during test and to a delivery line for said filtered fluid during use;

said vent means adapted at particular times to be selectively closed and connected to a source of controlled air pressure; and a flow condition indicating means communicating with the outlet area at the upper portion of said chamber, and having valve means for controlling flow through said indicating means.

2. The apparatus in accordance with claim 1 and
the periphery of said membrane filter extending outwardly of said chamber and being retained between said cover and said base.

3. The apparatus in accordance with claim 2, and said membrane filter comprising
a disc type filter membrane; and
a backing plate supporting said membrane and capable of permitting flow of fluid therethrough.

4. The apparatus in accordance with claim 3, and
a first O-ring seal disposed between said base and the periphery of said backing plate; and
a second O-ring seal disposed between said cover and the periphery of said membrane.

5. The apparatus in accordance with claim 4, and
said cover provided with a plurality of ribs extending into the outlet area of said chamber and engaging said backing plate thereby preventing deflection of said membrane filter due to pressure differential across said filter membrane.

6. The apparatus in accordance with claim 1, and
said membrane filter comprising a filter cartridge having membrane filter media sealed at its upper and lower ends, and a core through the filter media;
said cartridge being removably disposed in the inlet area of said chamber; and
said core defining the outlet area of said chamber and having an upper end connected to communicate with said flow condition indicating means and a lower end connected to communicate with said outlet.

7. The apparatus in accordance with claim 6, and
said indicating means and said outlet each providing a socket axially aligned with the socket provided by the other; and
said cartridge having a pair of end caps sealing the ends of said filter media and being inserted into said axially aligned sockets thereby providing communication between the outlet area of said chamber and said indicating means at the upper end of said core and said outlet at the lower end of said core.

8. The apparatus in accordance with claim 7, and
an axially spaced pair of O-ring seals engaging each of said end caps and said socket into which said end cap is inserted.

9. The apparatus in accordance with claim 8, and
said end cap at the upper end of said cartridge defining an axial flow path therethrough with a portion of larger diameter communicating with said core and a portion of smaller diameter communicating with said indicating means; and said axial flow path having a tapered intermediate portion flow connecting said portions of larger and smaller diameters to permit air bubbles to rise unimpeded from said core into said indicating means.

10. The apparatus in accordance with claim 1, and
a plurality of said indicating means each communicating with the outlet area at the upper portion of said chambers;
said membrane filter comprising a plurality of filter cartridges each having membrane filter media sealed at its upper and lower ends, and a core through the filter media;
said cartridges being removably disposed in the inlet area of said chamber and the cores of said cartridges defining the outlet area of said chamber; and
each of said cores having an upper end connected to communicate with a different one of said indicating means and a lower end connected to communicate with said outlet.

11. The apparatus in accordance with claim 10, and
a plurality of pairs of axially aligned sockets in communication with said chamber;
each of said indicating means providing one of said sockets of a different one of said pairs and the housing providing the other sockets of said pairs which communicate with each other and said outlet;
said cartridges each having a pair of end caps sealing the ends of said filter media and being inserted into a different one of said pairs of axially aligned sockets thereby providing communication between the outlet area of said chamber and said indicating means at the upper ends of said cores and said outlet at the lower ends of said cores.

12. The apparatus in accordance with claim 11, and
said end cap at the upper end of each of said cartridges defining an axial flow path therethrough with a portion of larger diameter communicating with the core of said cartridge and a portion of smaller diameter at the end of the cap communicating with one of said indicating means and
said axial flow path having an intermediate portion with a tapered wall connecting the portions with larger and smaller diameters together to permit air bubbles to rise unimpeded from said core into said indicating means.

13. The apparatus in accordance with claim 12, and
a different axially spaced pair of O-ring seals engaging each of said end caps and said socket into which said end cap is inserted.

14. A method of testing membrane type filter cartridges at the site of use, comprising the steps of
placing a plurality of cartridges in the chamber of a filter housing at the filtering site with the lower end of the core of each cartridge in communication with the outlet of the housing and the upper end of the core of each cartridge in communication with a different one of a plurality of flow condition indicating means which extend through the top of the housing;
with the outlet closed, venting the top of the chamber and opening the inlet to admit test liquid to fill the chamber;
closing the vent and opening the outlet to provide a continuous flow of test liquid from the inlet through all of the cartridges to the open outlet;
venting the indicating means one by one to sequentially fill each of the indicating means while maintaining flow through all of the cartridges until the membrane filter media thereof is thoroughly wet by the test liquid;

closing the inlet and connecting chamber to air pressure at about 5 psig to cause all of the test liquid to flow from the chamber through the membrane filter media of all of the cartridges while monitoring all of the indicating means to determine that no air bubbles appear therein;

increasing the air pressure slowly while monitoring all of the indicating means to determine that no air bubbles appear in quick sequence in any of the indicating means until the air pressure reaches the acceptable diffusional flow rate test pressure range as predetermined in accordance with the membrane filter media of the cartridges being tested; and draining all test liquid from the chamber, the indicating means and the cartridges.

15. The method in accordance with claim 14, and further increasing the air pressure before draining and substantially instantaneously replacing test liquid in all of the indicating means with air to determine the foam all-over point of the cartridges.

16. The method in accordance with claim 14 when air bubbles appear in an indicating means thereby indicating the cartridge in communication therewith is defective, comprising the further steps of venting the indicating means with air from air bubbles; and choking the flow through the outlet to maintain a column of test liquid in the vented indicating means until the test is completed.

17. A method of testing a filter with membrane filter media at the site of use, comprising the steps of placing a membrane filter in the chamber of a housing between inlet and outlet which communicate with the bottom of the chamber;

providing a flow condition indicating means in communication with the upper portion of said chamber on the outlet side of said membrane filter;

with the outlet closed; venting the upper portion of the chamber on the inlet side of said membrane filter and admitting test liquid into the inlet to fill the chamber;

closing the vent when test liquid fills the chamber and opening the outlet to provide a continuous flow of test liquid from the outlet through said membrane filter to the outlet;

venting the indicating means only until it is filled with test liquid and maintaining flow through the membrane filter until the membrane is thoroughly wet by the test liquid;

closing the inlet and connecting the inlet side of the chamber to a source of air pressure at about 5 psig while monitoring the indicating means to determine that no air bubbles appear therein;

increasing the air pressure slowly while monitoring the indicating means to determine that no air bubbles appear therein in quick sequence until the air pressure is in the acceptable diffusional flow rate test pressure range as predetermined by the membrane of the filter being tested;

disconnecting the air pressure and draining all test liquid from the chamber and the indicating means.

18. The method in accordance with claim 17, and comprising the step of venting the chamber and indicating means while connecting the inlet to a drain line for draining the chamber and the indicating means.

19. The method in accordance with claim 18, and further increasing the air pressure before draining and substantially instantaneously replacing test liquid in the indicating means with air to determine the foam all-over point of the membrane.

20. A method of testing membrane type filter cartridges at the site of use, comprising the steps of placing a cartridge in the chamber of a filter housing at the filtering site with its core in flow communication at its lower end with the outlet of the housing and at its upper end with a flow condition indicating means extending through the top of the housing;

with the outlet closed, venting the upper portion of the chamber and admitting test liquid into the inlet of the housing to fill the chamber;

closing the vent and opening the outlet to provide a continuous flow of test liquid from the inlet through the cartridge to the outlet;

venting the indicating means only until it is filled with test liquid and maintaining flow through the cartridge until the membrane media thereof is thoroughly wet by the test liquid;

closing the inlet and connecting the chamber to air pressure at about 5 psig to move all of the test liquid from the chamber through the membrane media while monitoring the indicating means to determine that no air bubbles appear therein;

increasing the air pressure slowly while monitoring the indicating means to determine that no air bubbles appear therein in quick sequence until the air pressure is in the acceptable diffusional flow rate test pressure range as predetermined in accordance with the membrane of the cartridge being tested; and draining all test liquid from the chamber, the indicating means and the cartridge.

21. The method in accordance with claim 20, and comprising the step of venting the chamber and the indicating means while connecting the inlet to a drain line for draining the chamber, indicating means and cartridge.

22. The method in accordance with claim 21, and further increasing the air pressure before draining and substantially instantaneously replacing test liquid in the indicating means with air to determine the foam all-over point of the cartridge.

* * * * *